US011517919B2

(12) United States Patent
Kusters et al.

(10) Patent No.: US 11,517,919 B2
(45) Date of Patent: Dec. 6, 2022

(54) SYSTEMS AND METHODS FOR HARVESTING MNCS AS PART OF A PLASMA COLLECTION PROCEDURE

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 397 days.

(21) Appl. No.: 16/880,022

(22) Filed: May 21, 2020

(65) Prior Publication Data

US 2020/0384482 A1 Dec. 10, 2020

Related U.S. Application Data

(60) Provisional application No. 62/857,890, filed on Jun. 6, 2019.

(51) Int. Cl.
*B04B 5/04* (2006.01)
*B01D 63/16* (2006.01)
*B04B 13/00* (2006.01)

(52) U.S. Cl.
CPC ............ *B04B 5/0442* (2013.01); *B01D 63/16* (2013.01); *B04B 13/00* (2013.01); *B04B 2005/0471* (2013.01)

(58) Field of Classification Search
CPC .................. B04B 5/0442; B04B 13/00; B04B 2005/0471
See application file for complete search history.

(56) References Cited

U.S. PATENT DOCUMENTS

| 4,776,964 | A | 10/1988 | Schoendorfer et al. |
| 5,194,145 | A | 3/1993 | Schoendorfer |
| 5,868,696 | A | 2/1999 | Giesler et al. |
| 6,027,657 | A | 2/2000 | Min et al. |
| 6,419,822 | B2 | 7/2002 | Muller et al. |
| 8,556,793 | B2 | 10/2013 | Foley et al. |
| 8,566,793 | B2 | 10/2013 | Ahadian et al. |
| 2018/0078699 | A1 | 3/2018 | Prendergast et al. |

FOREIGN PATENT DOCUMENTS

WO    WO2018/053217 A1    3/2018

OTHER PUBLICATIONS

European Patent Office, Extended European Search Report, counterpart EP Appl. No. 20177806 (dated Nov. 4, 2020) (6 pages).

*Primary Examiner* — Timothy C Cleveland
(74) *Attorney, Agent, or Firm* — Cook Alex Ltd.

(57) ABSTRACT

A blood separation system is provided that includes a blood separation device that includes a centrifugal separator and a spinning membrane separator drive unit incorporated into a common case and a fluid flow circuit having both a separation chamber configured to be mounted in the centrifugal separator of the blood separation device and a spinning membrane separator configured to be received in the spinning membrane separator drive unit. In an exemplary procedure, the system is used to collect concentrated platelets and/or concentrated platelets and plasma, and to further permit harvesting of the mononuclear cells from the centrifugal separator at the conclusion of platelet collection, and transfer of the mononuclear cells to the spinning membrane separator.

9 Claims, 9 Drawing Sheets

SYSTEMS AND METHODS FOR HARVESTING MNCS AS PART OF A PLASMA COLLECTION PROCEDURE

TECHNICAL FIELD

The present subject matter relates to systems and methods for processing and collecting blood, blood constituents, or other suspensions of cellular material. More particularly, the present subject matter relates to systems and methods employing both centrifugal and spinning membrane separation techniques for harvesting and storing mononuclear cells (MNCs) as part of a platelet collection procedure.

BACKGROUND

Various blood processing systems now make it possible to collect particular blood constituents, instead of whole blood, from a blood source. Typically, in such systems, whole blood (WB) is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

According to one approach, whole blood may be separated into its constituents through centrifugation. This requires that the whole blood be passed through a centrifuge after it is withdrawn from, and before it is returned to, the blood source. To reduce contamination and possible infection (if the blood source is a human donor or patient), the blood is preferably processed within a sealed, sterile fluid flow circuit during the centrifugation process. Typical disposable flow circuits include a separation chamber portion, which is mounted in cooperation on a durable, reusable assembly containing the hardware (centrifuge, drive system, pumps, valve actuators, programmable controller, and the like) that rotates the separation chamber and controls the flow through the fluid circuit.

The centrifuge rotates the separation chamber of the disposable flow circuit during processing, causing the heavier (greater specific gravity) components of the whole blood in the separation chamber, such as red blood cells, to move radially outwardly away from the center of rotation toward the outer or "high-G" wall of the separation chamber. The lighter (lower specific gravity) components, such as plasma, migrate toward the inner or "low-G" wall of the separation chamber. The boundary that forms between the heavier and lighter components in the separation chamber is commonly referred to as the interface. Various ones of these components can be selectively removed from the whole blood by providing appropriately located channeling structures and outlet ports in the flow circuit. For example, in one blood separation procedure, platelet rich plasma (PRP) may be separated from the other blood components and collected, with the non-targeted blood components and a replacement fluid being returned to the blood source.

There is another class of devices, based on the use of a membrane, that has been used for plasmapheresis (i.e., separating plasma from whole blood). More specifically, this type of device employs relatively rotating surfaces, at least one or which carries a porous membrane. Typically, the device employs an outer stationary housing and an internal spinning rotor covered by a porous membrane.

Well-known plasmapheresis devices include the Autopheresis-C® and Aurora separators sold by Fenwal, Inc, of Lake Zurich, Ill., which is an affiliate of Fresenius Kabi AG of Bad Homburg, Germany. A detailed description of an exemplary spinning membrane separator may be found in U.S. Pat. No. 5,194,145, which is incorporated by reference herein. This patent describes a membrane-covered spinner having an interior collection system disposed within a stationary shell. Blood is fed into an annular space or gap between the spinner and the shell. The blood moves along the longitudinal axis of the shell toward an exit region, with plasma passing through the membrane and out of the shell into a collection bag. The remaining blood components, primarily red blood cells, platelets, and white blood cells, move to the exit region between the spinner and the shell and then are typically returned to the donor.

More recently, integrated systems incorporating both centrifugal separation and spinning membrane separation have been developed. See, e.g., WO 2018/053217, which is incorporated herein by reference.

When such a system is used for platelet separation, white blood cells (WBCs), which include MNCs, build up in the separation chamber of the centrifuge between a red blood cell (RBC) layer and a PRP layer. Typically, these MNCs, along with the rest of the fluids in the separation chamber, are returned to the donor after completion of the platelet collection. However, it may be desirable to harvest these MNCs to form a small MNC product, which may then be used for, e.g., cell therapy research.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended.

In a first aspect, a method is provided for harvesting mononuclear cells (MNCs) during a platelet collection procedure comprising: a) withdrawing whole blood (WB) from a blood source; b) introducing WB into a centrifugal separator; c) separating WB within the centrifugal separator into platelet rich plasma (PRP), packed red blood cells (RBCs) containing WBCs and a WBC layer including MNCs; d) flowing PRP to a spinning membrane separator; e) flowing a first quantity of RBCs and WBCs to a return container; f) retaining a second quantity of RBCs and the WBCs, including MNCs, within the centrifugal separator; g) separating PRP within the spinning membrane separator into platelet poor plasma (PPP) and platelet concentrate (PC); h) flowing the PPP to one of the return container and a first collection container; i) flowing the PC to a second collection container; j) flowing RBCs, or RBCs and PPP, from the return container to the centrifugal separator in an amount sufficient to push the MNCs out of the centrifugal separator; k) flowing the MNCs to the spinning membrane separator; and l) sealing the spinning membrane separator to retain the MNCs therein.

In a second aspect, the method comprises flowing PPP from the spinning membrane separator after step k) to concentrate the MNCs within the spinning membrane separator.

In a third aspect, the method comprises adding platelet additive solution (PAS) to the second collection container after the PC has been flowed thereto.

In a fourth aspect, the method further comprises detecting whether a specified optical density of RBCs are exiting the centrifugal separator, and stopping step j) upon detecting the specified optical density of RBCs exiting the centrifugal separator.

In a fifth aspect, the spinning membrane separator is part of disposable fluid flow circuit, and the method further comprises detaching the sealed spinning membrane separator from the fluid flow circuit.

In a sixth aspect, a blood separation system is provided that comprises: 1) a disposable fluid flow circuit comprising a centrifugal separation chamber, a spinning membrane separator, a return container, a first collection container, and a second collection container, all interconnected by tubing to permit fluid flow therebetween; and 2) a hardware component comprising a centrifugal separator configured to receive the centrifugal separation chamber of the fluid flow circuit, a spinning membrane separator drive unit configured to receive the spinning membrane separator of the fluid flow circuit, and a controller configured and/or programmed to control the operation of the centrifugal separator and the spinning membrane separator drive unit,. The controller is configured and/or programmed to automatically a) withdraw whole blood (WB) from a blood source, b) introduce the WB into the centrifugal separation chamber, c) separate the WB within the centrifugal separation chamber into platelet rich plasma (PRP), packed red blood cells (RBCs) containing WBCs, and white blood cell (WBC) layer, including mononuclear cells (MNCs), d) flow PRP from the centrifugal separation chamber to the spinning membrane separator, e) flow a first quantity of RBCs and WBCs from the centrifugal separation chamber to the return container, f) retain a second quantity of RBCs and the WBCs, including MNCs, within the centrifugal separation chamber, g) separate the PRP with the spinning membrane separator into platelet poor plasma (PPP) and platelet concentrate (PC), h) flow the PPP from the spinning membrane separator to one of the return container and the first collection container, i) flow the PC from the spinning membrane separator to the second collection container, j) flow RBCs, or RBCs and PPP, from the return container to the centrifugal separation chamber in an amount sufficient to push the MNCs out of the centrifugal separation chamber, k) flow the MNCs to the spinning membrane separator, and l) retain the MNCs in the spinning membrane separator.

In a seventh aspect, the controller of the blood separation system is further configured and/or programmed to automatically: m) flow PPP from the spinning membrane separator to concentrate the MNCs within the spinning membrane separator.

In an eighth aspect, the disposable fluid flow circuit of the blood separation system further comprises a source of platelet additive solution (PAS) and the controller is further configured and/or programmed to automatically flow PAS to the second collection container after the PC has been flowed thereto.

In a ninth aspect, the hardware component of the blood separation system further comprises a sensor for detecting whether a specified optical density of RBCs are exiting the separation chamber and the programmer is further configured and/or programmed to automatically stop the flow RBCs, or RBCs and PPP, from the return container to the separation chamber upon detection of the specified optical density of RBCs exiting the separation chamber.

BRIEF DESCRIPTION OF THE DRAWINGS

FIGS. 3-9 are schematic views of the fluid flow circuit of FIG. 2 mounted on the blood separation device of FIG. 1, showing the system carrying out different fluid flow tasks in connection with separation and collection of platelets or platelets and plasma from blood, and to harvest the separated MNCs resulting from centrifugation. More specifically.

DETAILED DESCRIPTION OF THE ILLUSTRATED EMBODIMENTS

The embodiments disclosed herein are for the purpose of providing an exemplary description of the present subject matter. They are, however, only exemplary and not exclusive, and the present subject matter may be embodied in various forms. Therefore, specific details disclosed herein are not to be interpreted as limiting the subject matter as defined in the accompanying claims.

FIGS. 1-9 show components of a blood or fluid separation system that embodies various aspects of the present subject matter. While the system may be referred to herein as a "blood processing system" or a "blood separation system" and examples will be given of various ways in which the system may be used to separate blood into its component parts, it should be understood that systems according to the present disclosure can be used for processing a variety of fluids, which may include bodily fluids and non-bodily fluids.

Figure 1:
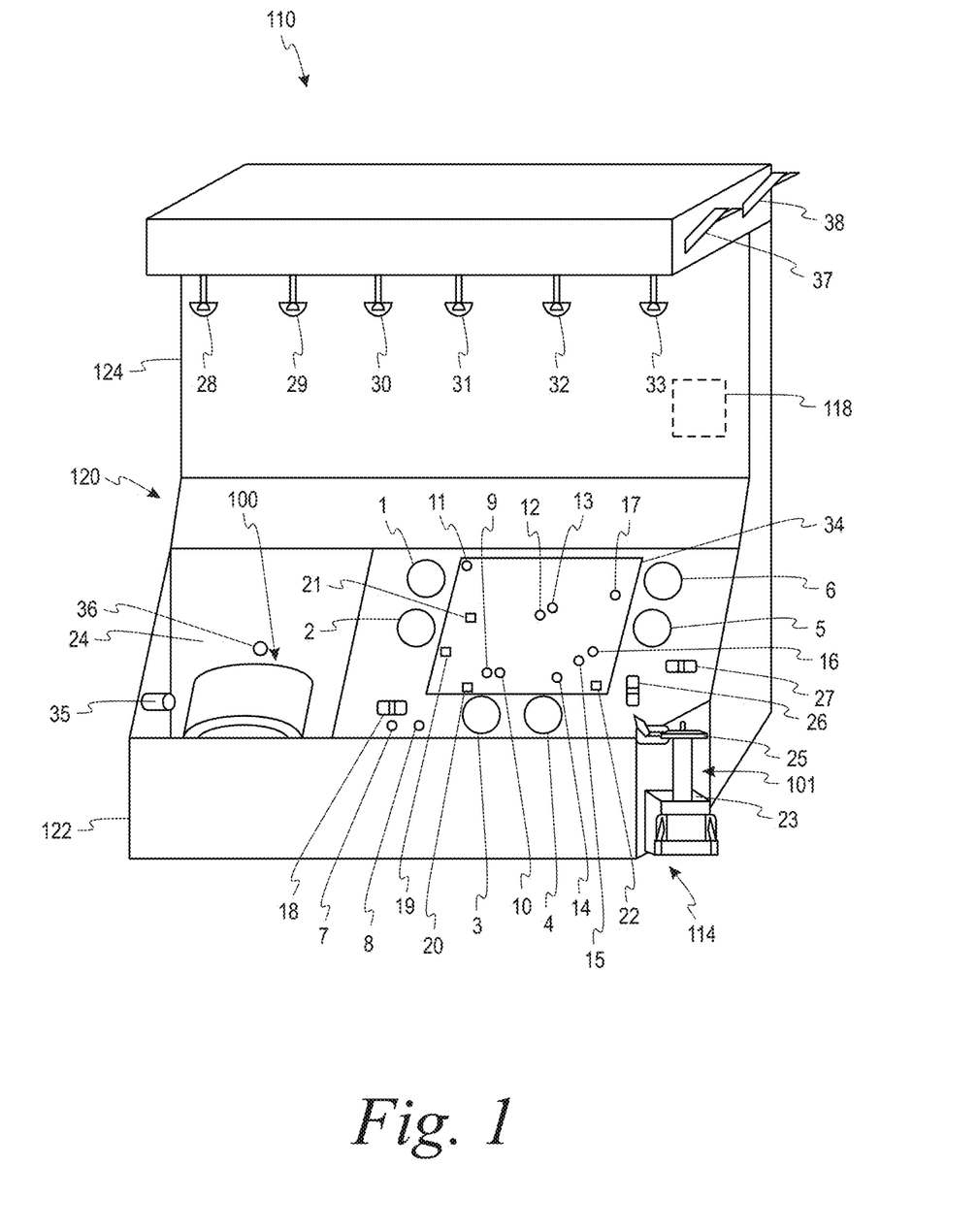
FIG. 1 is a perspective view of an exemplary blood separation device including both centrifugal and spinning membrane separation technologies, and that that comprises a component of a blood separation system according to an aspect of the present disclosure.
Figure 2:
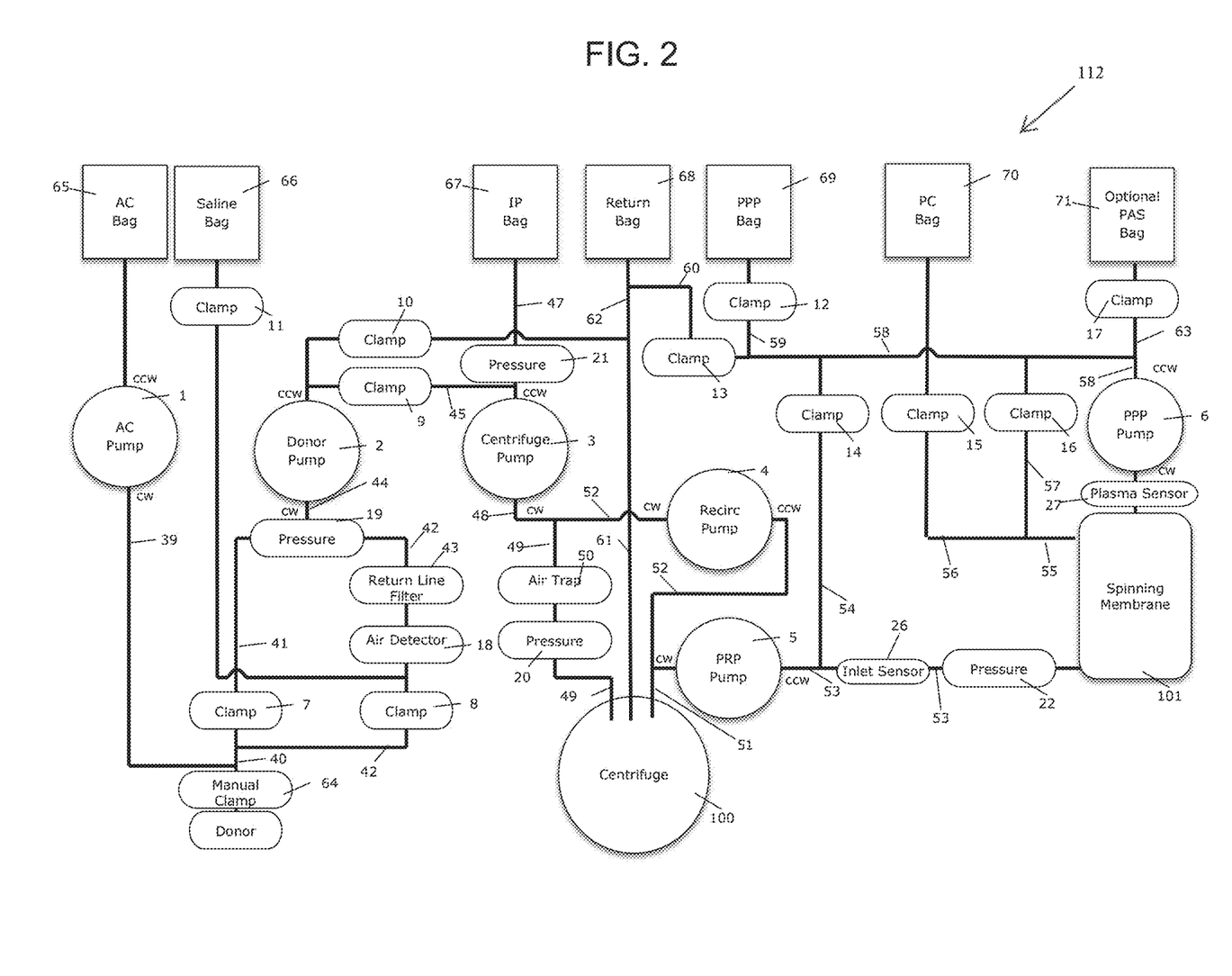
FIG. 2 is a schematic view of an exemplary disposable fluid flow circuit utilizing a single needle (SN) for collecting platelet concentrate (PC) or PC and platelet poor plasma (PPP) mounted to the blood separation device of FIG. 1.

Generally speaking, the system includes two principal components, a durable and reusable blood separation device (FIG. 1) and a disposable fluid flow circuit (FIG. 2). The blood separation device includes a spinning membrane separator drive unit, a centrifuge or centrifugal separator, additional components that control fluid flow through the disposable flow circuit, and a controller, which governs the operation of the other components of the blood separation device to perform a blood processing and collection procedure, as will be described in greater detail.

I. The Durable Blood Separation Device

The blood separation device 110 (best seen in FIG. 1) is configured as a durable item that is capable of long-term use. It should be understood that the blood separation device 110 of FIG. 1 is merely exemplary of one possible configuration and that blood separation devices according to the present disclosure may be differently configured.

In the illustrated embodiment, the blood separation device 110 is embodied in a single housing or case 120. The illustrated case includes a generally horizontal portion 122 (which may include an inclined or angled face or upper surface for enhanced visibility and ergonomics) and a generally vertical portion 124. The spinning membrane separator drive unit 114 and the centrifugal separator 100 are shown as being incorporated into the generally horizontal portion of the case, while the controller 118 is typically incorporated into the generally vertical portion. The configuration and operation of the spinning membrane separator drive unit 114, the centrifugal separator 100, the controller 118, and selected other components of the blood separation device will be described below in greater detail.

A. Spinning Membrane Separator Drive Unit

The blood separation device includes a spinner support or spinning membrane separator drive unit 114 for accommodating a generally cylindrical spinning membrane separator 101 of the fluid flow circuit. U.S. Pat. No. 5,194,145 describes an exemplary spinning membrane separator drive unit that would be suitable for incorporation into the blood separation device, but it should be understood that the spinning membrane separator drive unit may be differently configured without departing from the scope of the present disclosure.

The illustrated spinning membrane separator drive unit has a base 23 configured to receive a lower portion of the spinning membrane separator 101 and an upper end cap 25 to receive an upper portion of the spinning membrane separator 101. Preferably, the upper end cap 25 is positioned directly above the base 23 to orient a spinning membrane separator 101 received by the spinning membrane separator drive unit vertically and to define a vertical axis about which the spinning membrane separator 101 is spun. While it may be advantageous for the spinning membrane separator drive unit to vertically orient a spinning membrane separator 101, it is also within the scope of the present disclosure for the spinning membrane separator 101 to be differently oriented when mounted to the blood separation device 110.

In one embodiment, one of the base 23 and upper end cap 25 of the spinning membrane separator drive unit 114 is movable with respect to the other, which may allow differently sized spinning membrane separators 101 to be received by the spinning membrane separator drive unit. For example, the upper end cap 25 may be translated vertically with respect to the base 23 and locked in a plurality of different positions, with each locking position corresponding to a differently sized spinning membrane separator 101.

At least one of the base 23 and the upper end cap 25 is configured to spin one or more components of the spinning membrane separator 101 about the axis defined by the spinning membrane separator drive unit. The mechanism by which the spinning membrane separator drive unit spins one or more components of the spinning membrane separator 101 may vary without departing from the scope of the present disclosure. In one embodiment, a component of the spinning membrane separator 101 to be spun includes at least one element configured to be acted upon by a magnet (e.g., a metallic material), while the spinning membrane separator drive unit includes a magnet (e.g., a series of magnetic coils or semi-circular arcs). By modulating the magnetic field acting upon the aforementioned element of the spinning membrane separator 101, the component or components of the spinning membrane separator 101 may be made to spin in different directions and at varying speeds. In other embodiments, different mechanisms may be employed to spin the component or components of the spinning membrane separator 101.

Regardless of the mechanism by which the spinning membrane separator drive unit spins the component or components of the spinning membrane separator 101, the component or components of the spinning membrane separator 101 is preferably spun at a speed that is sufficient to create Taylor vortices in a gap between the spinning component and a stationary component of the spinning membrane separator 101 (or a component that spins at a different speed). Fluid to be separated within the spinning membrane separator 101 flows through this gap, and filtration may be dramatically improved by the creation of Taylor vortices.

B. Centrifugal Separator

As for the centrifugal separator, it includes a centrifuge compartment 24 that receives a centrifugal separation chamber 100, as well as other components of the centrifugal separator. Further details as to the centrifugal separator are set forth in WO 2018/053217, referenced and incorporated herein by reference above.

Blood is introduced into the centrifugal separation chamber 100 by an umbilicus, with the blood being separated (e.g., into a layer of less dense components, such as platelet-rich plasma, and a layer of more dense components, such as packed red blood cells and white blood cells) within the centrifugal separation chamber 100 as a result of centrifugal forces as it rotates. Components of an interface monitoring system may be positioned within the centrifuge compartment 24 to oversee separation of blood within the centrifugal separation chamber. The interface monitoring system may include a light source 35 and a light detector 36, which is positioned and oriented to receive at least a portion of the light emitted by the light source 35.

The generally horizontal portion of the case 122 of the illustrated blood separation device 10 includes a cassette station 34, which accommodates a flow control cassette of the fluid flow circuit 112. In one embodiment, the cassette station 34 is similarly configured to the cassette station of U.S. Pat. No. 5,868,696 (which is incorporated herein by reference), but is adapted to include additional components and functionality. The illustrated cassette station 34 includes a plurality of clamps or valves 9-17, which move between a plurality of positions to selectively contact or otherwise interact with corresponding valve stations of the flow control cassette of the fluid flow circuit.

In the actuated position, a valve 9-17 engages the associated valve station to prevent fluid flow through that valve station (e.g., by closing one or more ports associated with the valve station, thereby preventing fluid flow through that port or ports). In the retracted position, a valve 9-17 is disengaged from the associated valve station (or less forcefully contacts the associated valve station than when in the actuated position) to allow fluid flow through that valve station (e.g., by opening one or more ports associated with the valve station, thereby allowing fluid flow through that port or ports). Additional clamps or valves 7 and 8 may be positioned outside of the cassette station 34 to interact with portions of valve stations (which may be lengths of tubing) of the fluid flow circuit to selectively allow and prevent fluid flow therethrough. The valves 9-17 and corresponding valve stations of the cassette station 34 and cassette may be differently configured and operate differently from the valves 7 and 8 and the valve stations that are spaced away from the cassette station 34.

The cassette station 34 may be provided with additional components, such as pressure sensors 19-22, which interact with sensor stations of the cassette to monitor the pressure at various locations of the fluid flow circuit. For example, if the blood source is a human donor, one or more of the pressure sensors 19-22 may be configured to monitor the pressure of the donor's vein during blood draw and return. Other pressure sensors 19-22 may monitor the pressure of the spinning membrane separator 101 and the centrifugal separation chamber 100. The controller may receive signals from the pressure sensors 19-22 that are indicative of the pressure within the fluid flow circuit and, if a signal indicates a low- or high-pressure condition, the controller may initiate an alarm or error condition to alert an operator to the condition and/or to attempt to bring the pressure to an acceptable level without operator intervention.

The blood separation device may also include a plurality of pumps 1-6 to cause fluid to flow through the fluid flow circuit. The pumps 1-6 may be differently or similarly configured and/or function similarly or differently from each other. In the illustrated embodiment, the pumps 1-6 are configured as peristaltic pumps, which may be generally configured as described in U.S. Pat. No. 5,868,696. Each pump 1-6 engages a different tubing loop extending from a side surface of the flow control cassette and may be selectively operated under command of the controller to cause fluid to flow through a portion of the fluid flow circuit, as will be described in greater detail below. In one embodiment, all or a portion of the cassette station 34 may be capable of translational motion in and out of the case to allow for automatic loading of the tubing loops into the associated pump 1-6.

The illustrated blood separation device also includes a spinner inlet sensor 26 for determining one or more properties of a fluid flowing into a spinning membrane separator 101 mounted within the spinning membrane separator drive unit. If the fluid flowing into the spinning membrane separator 101 is whole blood (which may include anticoagulated whole blood), the spinner inlet sensor 26 may be configured to determine the hematocrit of the blood flowing into the spinning membrane separator 101. If the fluid flowing into the spinning membrane separator 101 is platelet-rich plasma, the spinner inlet sensor 26 may be configured to determine the platelet concentration of platelet-rich plasma flowing into the spinning membrane separator 101. The spinner inlet sensor 26 may detect the one or more properties of a fluid by optically monitoring the fluid as it flows through tubing of the fluid flow circuit, or by any other suitable approach. The controller may receive signals from the spinner inlet sensor 26 that are indicative of the one or more properties of fluid flowing into the spinning membrane separator 101 and use the signals to optimize the separation procedure based upon that property or properties. If the property or properties is/are outside of an acceptable range, then the controller may initiate an alarm or error condition to alert an operator to the condition. A suitable device and method for monitoring hematocrit and/or platelet concentration is described in U.S. Pat. No. 6,419,822 (which is incorporated herein by reference), but it should be understood that a different approach may also be employed for monitoring hematocrit and/or platelet concentration of fluid flowing into the spinning membrane separator 101.

The illustrated blood separation device further includes a spinner outlet sensor 27, which accommodates tubing of the fluid flow circuit that flows a separated blood component out of the spinning membrane separator 101. The spinner outlet sensor 27 monitors the fluid to determine one or more properties of the fluid, and may do so by optically monitoring the fluid as it flows through the tubing or by any other suitable approach. In one embodiment, separated plasma flows through the tubing, in which case the spinner outlet sensor 27 may be configured to determine the amount of cellular blood components in the plasma and/or whether the plasma is hemolytic and/or lipemic. This may be done using an optical monitor of the type described in U.S. Pat. No. 8,556,793 (which is incorporated herein by reference) that measures the optical density of the fluid in the associated tubing, or by any other suitable device and/or method.

The illustrated blood separation device also includes an air detector 18 (e.g., an ultrasonic bubble detector), which accommodates tubing of the fluid flow circuit that flows fluid to a recipient. It may be advantageous to prevent air from reaching the recipient, whether a human recipient (e.g., the same human that serves as the blood source) or a non-human recipient (e.g., a storage bag or container), so the air detector 18 may transmit signals to the controller that are indicative of the presence or absence of air in the tubing. If the signal is indicative of air being present in the tubing, the controller may initiate an alarm or error condition to alert an operator to the condition and/or to take corrective action to prevent the air from reaching the recipient (e.g., by reversing the flow of fluid through the tubing or diverting flow to a vent location).

The generally vertical portion of the case may include a plurality of weight scales 28-33 (six are shown, but more or fewer may be provided), each of which may support one or more fluid containers 65-71 of the fluid flow circuit (FIGS. 2-9). The containers 65-71 receive blood components separated during processing or intravenous fluids or additive fluids. Each weight scale 28-33 transmits to the controller a signal that is indicative of the weight of the fluid within the associated container 65-71 to track the change of weight during the course of a procedure. This allows the controller to process the incremental weight changes to derive fluid processing volumes and flow rates and subsequently generate signals to control processing events based, at least in part, upon the derived processing volumes. For example, the controller may diagnose leaks and obstructions in the fluid flow circuit and alert an operator.

The illustrated case 120 is also provided with a plurality of hooks or supports 37 and 38 that may support various components of the fluid flow circuit 12 or other suitably sized and configured objects.

C. Controller

According to an aspect of the present disclosure, the blood separation device includes a controller 118, which is suitably configured and/or programmed to control operation of the blood separation device. In one embodiment, the controller comprises a main processing unit (MPU), which can comprise, e.g., a Pentium™ type microprocessor made by Intel Corporation, although other types of conventional microprocessors can be used. In one embodiment, the controller may be mounted inside the generally vertical portion of the case, adjacent to or incorporated into an operator interface station (e.g., a touchscreen). In other embodiments, the controller and operator interface station may be associated with the generally horizontal portion or may be incorporated into a separate device that is connected (either physically, by a cable or the like, or wirelessly) to the blood separation device.

The controller 118 is configured and/or programmed to execute at least one blood processing application but, more advantageously, is configured and/or programmed to execute a variety of different blood processing applications. For example, the controller may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, and a platelet/plasma collection procedure. In the context of the present disclosure, the controller is programmed to carry out platelet collection procedures in which the MNCs are harvested at the conclusion of the procedures, as will be described in greater detail below.

More particularly, in carrying out these blood processing applications, the controller is configured and/or programmed to control one or more of the following tasks: drawing blood into a fluid flow circuit mounted to the blood separation device, conveying blood through the fluid flow circuit to a location for separation (i.e., into a spinning membrane separator 101 or centrifugal separation chamber 100 of the fluid flow circuit), separating the blood into two or more components as desired, and conveying the separated components into storage containers, to a second location for further separation (e.g., into whichever of the spinning membrane separator 101 and centrifugal separation chamber 100 that was not used in the initial separation stage), or to a recipient (which may be a donor from which the blood was originally drawn).

This may include instructing the spinning membrane separator drive unit and/or the centrifugal separator to operate at a particular rotational speed and instructing a pump 1-6 to convey fluid through a portion of the fluid flow circuit at a particular flow rate. Hence, while it may be described herein that a particular component of the blood separation device (e.g., the spinning membrane separator drive unit or the centrifugal separator) performs a particular function, it should be understood that that component is being controlled by the controller 118 to perform that function.

As will be described, the procedure described herein calls for the use of both the centrifugal separator and the spinning membrane separator drive unit, in which case a properly programmed controller is especially important to coordinate the operation of these two components, along with the other components of the blood separation device to ensure that flow to and from the centrifugal separation chamber 100 and spinning membrane separator 101 is at the proper level and that the components are functioning properly to process the blood circulating through the fluid flow circuit.

Before, during, and after a procedure, the controller 118 may receive signals from various components of the blood separation device (e.g., the pressure sensors 19-22) to monitor various aspects of the operation of the blood separation device and characteristics of the blood and separated blood components as they flow through the fluid flow circuit. If the operation of any of the components and/or one or more characteristics of the blood or separated blood components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 118 may include an interface control module, which receives signals from the light detector 36 of the interface monitoring system. The signals that the controller receives from the light detector 36 are indicative of the location of an interface between the separated blood components within the centrifugal separation chamber 100. If the controller determines that the interface is in the wrong location, then it can issue commands to the appropriate components of the blood separation device to modify their operation so as to move the interface to the proper location. For example, the controller may instruct one of the pumps 1-6 to cause blood to flow into the centrifugal separation chamber 100 at a different rate and/or for a separated blood component to be removed from the centrifugal separation chamber 100 at a different rate and/or for the centrifugal separation chamber 100 to be spun at a different speed by the centrifugal separator.

Such control typically occurs regardless of whether the blood originates from a container or directly from a donor, and regardless of whether the components are directed into storage containers or returned to a donor or another living recipient.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It is also within the scope of the present disclosure for the operator interface station to receive input from both a touchscreen and a separate input device, such as a keypad.

II. The Disposable Fluid Flow Circuit

A. Overview

As for the fluid flow circuit or flow set 112 (best seen in FIG. 2), it is intended to be a sterile, single use, disposable item. Before beginning a given blood processing and collection procedure, the operator loads various components of the fluid flow circuit in the case in association with the blood separation device. The controller implements the procedure based upon preset protocols, taking into account other input from the operator. Upon completing the procedure, the operator removes the fluid flow circuit from association with the blood separation device. The portions of the fluid flow ircuit holding the collected blood component or components (e.g., collection containers or bags) are removed from the case and retained for storage, transfusion, or further processing. The remainder of the fluid flow circuit is removed from the case and discarded.

Generally speaking, though, the fluid flow ircuit 112 includes a cassette, to which the other components of the fluid flow circuit are connected by flexible tubing. The other components may include a plurality of fluid containers 65-71. In the context of the present disclosure these containers include an anticoagulant container (65), a saline container (66), an In-Process container (67), a return container (68) a PPP container (69), a PC container (70), and a (optional) PAS container (71). The flow circuit further includes one or more blood source access devices (e.g., a connector for accessing blood within a fluid container or a phlebotomy needle), and a spinning membrane separator 101 and a centrifugal separation chamber 100.

B. Flow Control Cassette and Tubing

The flow control cassette provides a centralized, programmable, integrated platform for all the pumping and many of the valving functions required for a given blood processing procedure. In one embodiment, the cassette is similarly configured to the cassette of U.S. Pat. No. 5,868,696, but is adapted to include additional components (e.g., more tubing loops) and functionality.

In use, the cassette is mounted to the cassette station 34 of the blood separation device so as to align its sensor stations with an associated pressure sensor 19-22 of the cassette station 34, and its valve stations with an associated valve 9-17, and may define one or more ports that allow fluid communication between the valve stations and another interior cavity of the cassette (e.g., a flow path). As described above, each valve 9-17 is movable under command of the controller to move between a plurality of positions (e.g., between a retracted or lowered position and an actuated or raised position) to selectively contact the valve stations of the cassette. In the actuated position, a valve 9-17 engages the associated valve station to close one or more of its ports to prevent fluid flow therethrough. In the retracted position, a valve 9-17 is disengaged from the associated valve station (or less forcefully contacts the associated valve station than when in the actuated position) to open one or more ports associated with the valve station, thereby allowing fluid flow therethrough.

A plurality of tubing loops extend from the side surface of the cassette to interact with pumps 1-6 of the blood separation device 10. The different pumps 1-6 may interact with the tubing loops of the cassette to perform different tasks during a separation procedure (as will be described in greater detail), but in the context of the present disclosure, a different one of the pumps 1-6 may be configured to serve as an anticoagulant pump (1), a source/donor pump (2), a centrifuge pump (3), a recirculation pump (4), a PRP pump (5), and a PPP pump (6).

Additional tubing extends from the side surface of the cassette to connect to the other components of the fluid flow circuit 12, such as the various fluid containers 65-71, the spinning membrane separator 101, and the centrifugal separation chamber 100. The tubing connected to the centrifugal separator chamber 100 (which includes one inlet tube and two outlet tubes) may be aggregated into an umbilicus.

Various additional components may be incorporated into the tubing. For example, a manual clamp 64 may be associated with a line or lines leading to the blood source/donor, a return line filter 43 (e.g., a microaggregate filter) may be associated with a line leading to a fluid recipient, and/or an air trap 50 may be positioned on a line upstream of the centrifugal separation chamber 100.

III. Exemplary Platelet Collection Procedure

An exemplary platelet collection procedure with MNC harvest according to the present disclosure will now be described.

Prior to processing, an operator selects the desired protocol (e.g., using an operator interface station, if provided), which informs the controller of the manner in which it is to control the other components of the blood separation device during the platelet collection procedure. In the context of a platelet collection procedure, this includes whether plasma is also being collected, rather than being returned to the donor.

If the blood source is a donor, the operator may proceed to enter various parameters, such as the donor gender/height/weight. In one embodiment, the operator also enters the target yield for the various blood components (which may also include entering a characteristic of the blood, such as a platelet pre-count) or some other collection control system (e.g., the amount of whole blood to be processed).

If there are any fluid containers (e.g., a platelet additive solution container) that are not integrally formed with the fluid flow circuit, they may be connected to the fluid flow circuit (e.g., by piercing a septum of a tube of the fluid flow circuit 12 or via a luer connector), with the fluid flow circuit then being mounted to the blood separation device (including the fluid containers being hung from the weight scales 28-33, as appropriate). An integrity check of the fluid flow circuit may be executed by the controller to ensure the various components are properly connected and functioning. Following a successful integrity check, the blood source is connected to the fluid flow circuit (e.g., by connecting to a container of previously collected whole blood or by phlebotomizing a donor), and the fluid flow circuit may be primed (e.g., by saline pumped from a saline container 66 by operation of one or more of the pumps 1-6 of the blood separation device).

After the fluid flow circuit has been primed, blood separation may begin. The stages of blood separation vary depending on the particular procedure, and will be described in greater detail below.

According to one aspect of the present disclosure, the blood separation device 10 may be used to separate and collect platelets and substantially cell-free plasma from blood. If the source of whole blood is a donor, a blood separation device according to the present disclosure may be used in combination with a fluid flow circuit having a single blood access device (e.g., a single needle that draws blood from and returns a separated blood component to the same location). However, a fluid flow circuit having two blood access devices (e.g., one needle that draws blood from a source and a second needle that flows a separated blood component to the same source or to a different recipient) may also be used.

FIG. 2 is a schematic view of an exemplary fluid flow circuit 112 having a single blood access device (e.g., a connector for connecting to a container of previously collected whole blood or a single needle that draws blood from and returns a separated blood component to the same location) that may be used to separate and collect only platelets or both platelets and plasma. While the exemplary procedure is being described in the context of a flow circuit having a single blood access device, the MNC harvesting techniques described herein can also be performed using a flow circuit having two blood access devices. The fluid flow circuit includes a cassette of the type described above, which connects the various components of the fluid flow circuit. The various connections amongst the components of the fluid flow circuit are shown in FIG. 2, which also shows the fluid flow circuit mounted to the blood separation device.

All of the various valves 7-17 and pressure sensors 19-22 of the blood separation device are used in combination with the fluid flow circuit of FIG. 2 for separating and collecting platelets or platelets and plasma, except for pressure sensor 21. As will be described, fluid may flow through the sensor station associated with pressure sensor 21, but the pressure sensor 21 does not communicate with the controller to monitor the pressure at any location within the fluid flow circuit. Additionally, both the centrifugal separator and the spinning membrane separator drive unit are used in separating blood into platelets and plasma, and for harvesting the MNCs afterwards.

a. Draw Phase

Figure 3:
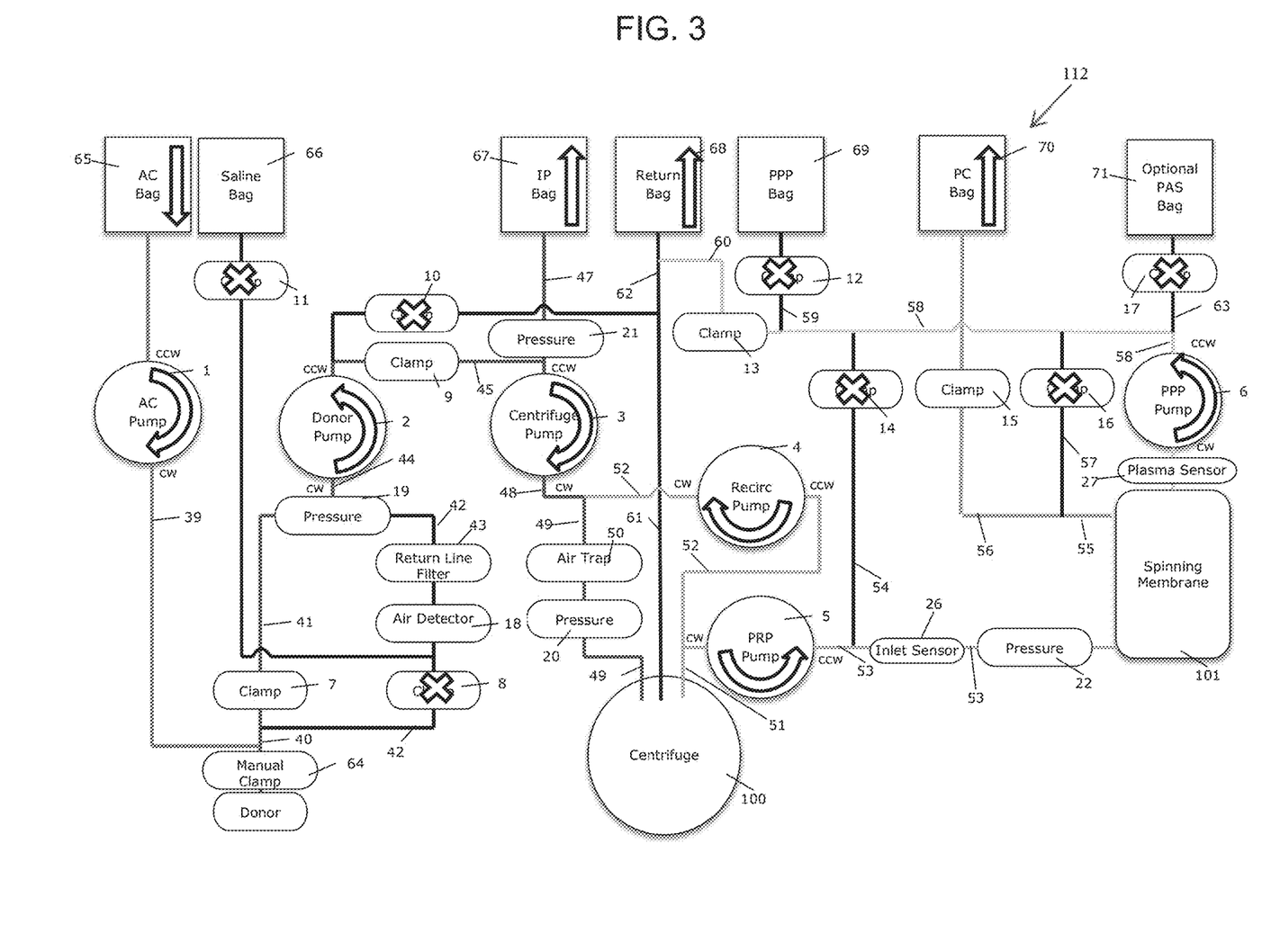
FIG. 3 depicts the draw phase of the procedure.

FIG. 3 displays the draw phase hardware state and flow paths. During the draw phase, donor pump 2 draws WB from the donor through manual clamp 64 into donor line 40. Anticoagulant (AC) is removed from AC bag 65 via AC pump 1 through AC line 39 and into donor line 40. The anticoagulated WB, which will be referred to simply as WB from this point forward, travels via donor pump 2 through draw line 41, pressure sensor 19 (vein pressure monitor), donor pump line 44, open clamp 9, and line 45.

Centrifuge pump 3 pushes WB through line 48, line 49, air trap 50, and pressure sensor 20 (centrifuge pressure monitor) into the centrifuge 100. The centrifuge pump 3 flow rate is less than the donor pump 2 flow rate, and the difference is the rate at which WB travels through line 47 into in process (IP) bag 67. WB is stored in the IP bag 67 to be used during the return phase. Pressure sensor 21 is not used during SN procedures.

In centrifuge 100, the WB is separated into PRP and packed RBCs. Centrifuge 100 rotates nominally at 4500 rpm but may vary depending on flow rates. WBCs, such as MNCs, may be retained within the centrifuge 100 or WBCs, such as granulocytes, may exit with the packed RBCs. The RBCs exit the centrifuge 100 through line 61.

PRP is drawn out of the centrifuge 100 through line 51 by PRP pump 5 and recirculation pump 4. The recirculation pump moves PRP through line 52 back to the inlet line 49 to decrease the HCT of the WB entering the centrifuge 100 to improve separation efficiency. Thus, the flow rate of the WB entering the centrifuge equals the centrifuge pump 2 rate plus the circulation pump 4 rate. Since the fluid drawn out of the centrifuge 100 into the PRP line 51 by the recirculation pump 4 is immediately added back into the centrifuge, the bulk or net PRP rate out of the centrifuge is equal to the rate of the PRP pump 5.

PRP is pumped through line 53, spinner inlet sensor 26, and pressure sensor 22 (spinner pressure monitor) into spinning membrane separator 101, which rotates nominally at 1500 rpm but may vary depending on flow rates. The inlet sensor 26 measures the concentration of platelets entering the spinner 101. Line 54 and clamp 14 act as a pathway to divert fluid exiting the centrifuge 100 towards the return bag 68 if necessary. An example would be at the start of a procedure when separation is initializing and platelets are not yet exiting the centrifuge 100, then the fluid traveling through PRP pump 5 would be diverted.

The spinning membrane separator 101 contains a membrane with pores smaller than the size of platelets (ex. 0.65 um nylon or 0.8 um polycarbonate membrane). Thus, only platelet poor plasma (PPP) is capable of passing through the membrane, PPP is pumped out of the spinning membrane 101 by PPP pump 6, passing through plasma sensor 27, line 58, open clamp 13, and line 60 into line 62 where the PPP is combined with RBCs from line 61 and the combined fluid enters return bag 68. Plasma line sensor 27 monitors the plasma for free hemoglobin and lipid concentrations. Clamp 12 is typically always closed during the draw phase. The difference between the spinner inlet rate of PRP pump 5 and the outlet rate of PPP pump 6 equals the rate at which the concentrated platelets will exit the spinner through line 55, line 56, and open clamp 15 and into the PC product bag 70. Line 57 and clamp 16 act as a pathway to divert fluid exiting the spinner to the return bag 68 if necessary. The concentration of the PC exiting the spinner is dependent on the PRP pump 5 rate, the PRP concentration, and the PPP pump 6 rate per the following relationship:

$$\text{PC Concentration} = (\text{PRP Concentration} * \text{PRP Inlet Rate})/(\text{PRP Inlet Rate} - \text{PPP Outlet Rate}) \quad [\text{Eq. 1}]$$

The draw phase continues until the amount of blood drawn from the blood source reaches a target amount or the in-process bag 67 is filled to a particular level (as determined by the weight scale from which the in-process bag is hung during the procedure) or until some other condition is satisfied. Then, the system will transition to the return phase.

b. Return Phase

Figure 4:
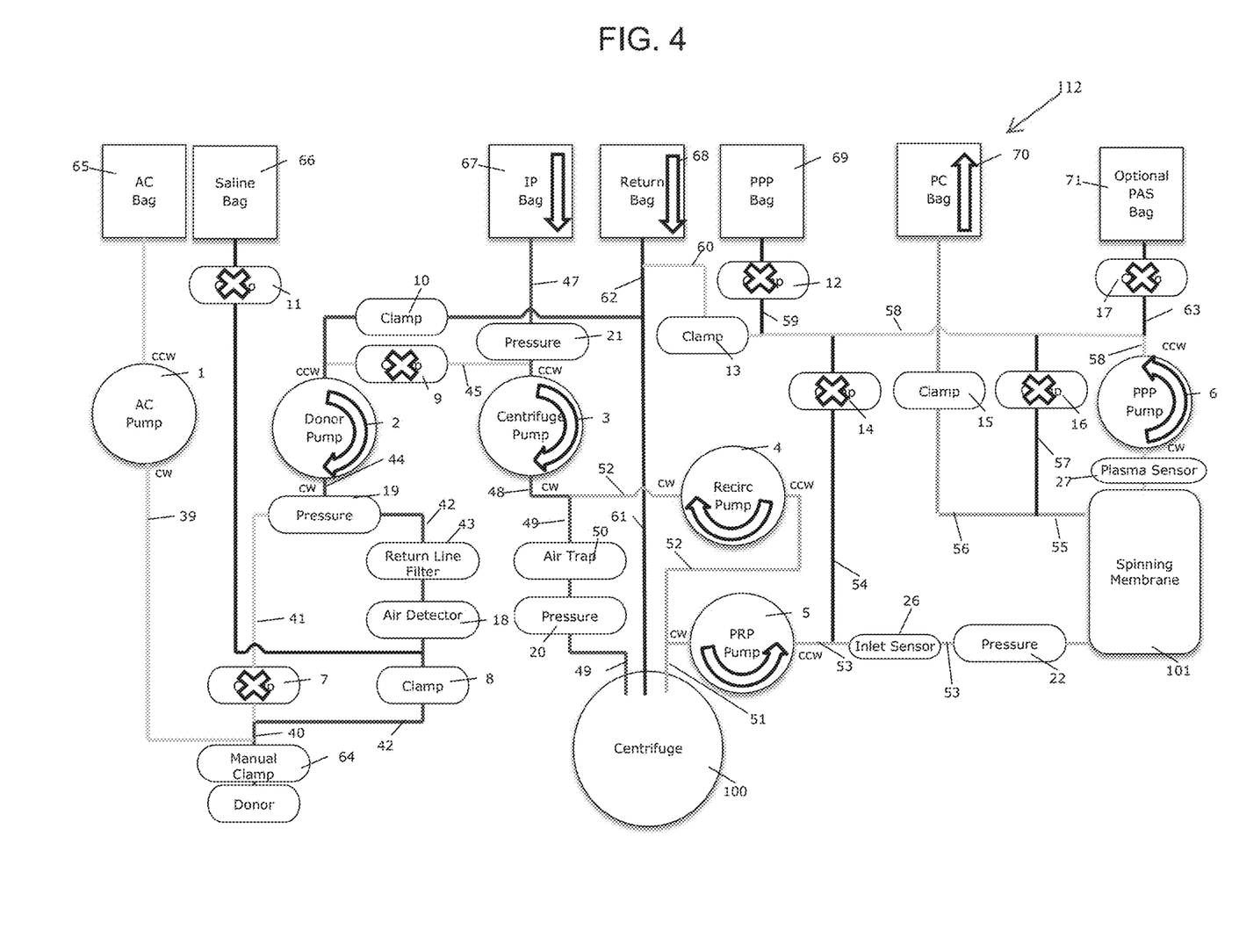
FIG. 4 depicts a return phase without PPP collection.
Figure 5:
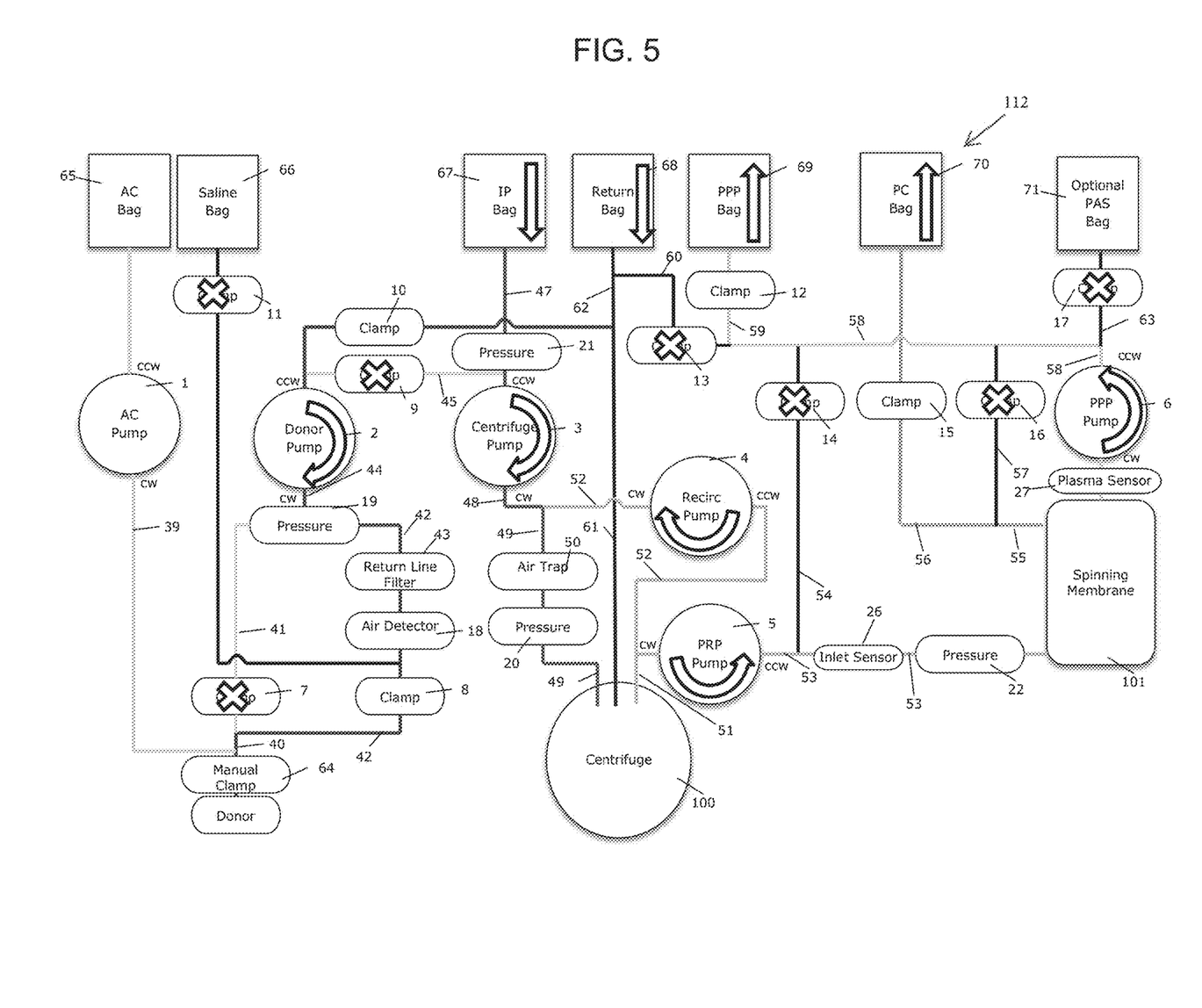
FIG. 5 depicts a return phase with PPP collection.

FIGS. 4 and 5 display the hardware state and flow paths for return phase without and with plasma collection, respectively. The WB that was stored in IP bag 67 during the draw cycles acts as the WB supply for the centrifuge during return. When the system transitions to the return phase, the centrifuge pump 3 remains unchanged and separation continues in the same manner as described for the draw cycle above, with WB emptying from the IP bag 67. Therefore, the system components downstream from the centrifuge pump are "blinded" as to whether the system is in draw or return.

For a procedure in which a concurrent PPP product collection is not desired, clamp 12 remains closed for the duration of the procedure. For a procedure in which a concurrent PPP product is desired, clamp 12 opens and clamp 13 will close at particular points in the return phase to allow for PPP collection through line 59 into PPP bag 69, as shown in FIG. 5.

When the system transitions to the return phase the AC pump 1 stops introducing AC. Clamp 7 closes to prevent fluid flow through line 41 and clamp 8 opens to allow fluid flow through line 42. Donor pump 2 reverses direction. Clamp 9 closes to prevent fluid flow through line 45. Clamp 10 opens to allow blood in the return bag 68 to be returned to the donor. Blood flows from the return bag 68 through line 62 where it is mixed with PPP coming from line 60 and RBC coming from line 61 as separation continues.

The rate at which donor pump 2 returns fluid to the donor is greater than the combined rates of RBC flowing into line 61 from the centrifuge 100 and PPP flow via PPP pump 6 allowing for the return bag to empty even though additional fluid is introduced to line 62 throughout return phase. The return blood is pumped through line 46, open clamp 10, line 44, line 42, pressure sensor 19 (vein pressure monitor), return line filter 43, air detector 18, open clamp 8, and line 40 on its way back to the donor. Once the return bag 68 is empty, the system transitions back to draw.

c. Optional PAS Addition

Figure 6:
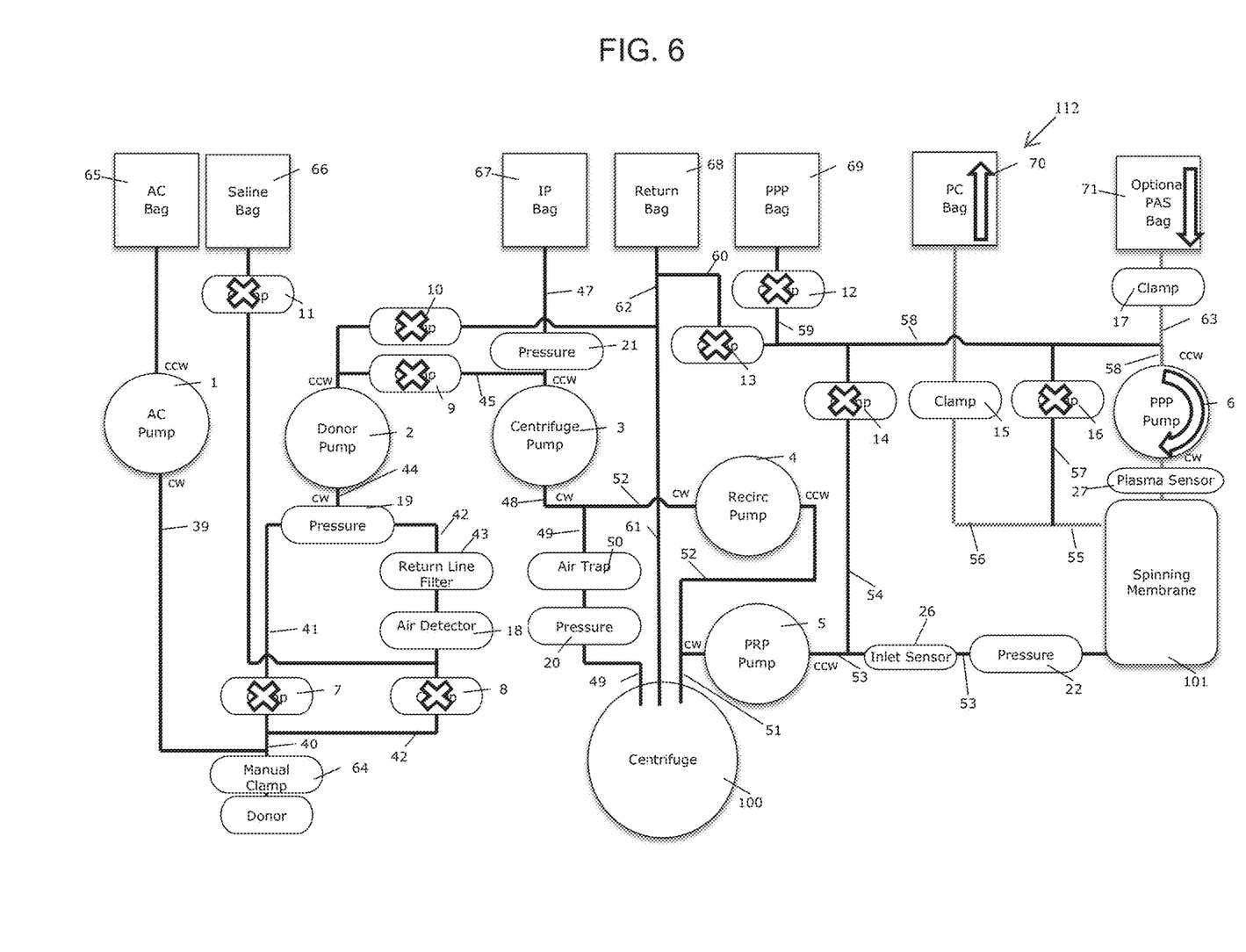
FIG. 6 illustrates an optional phase in which platelet additive solution (PAS) is added to the PC product.

When the targeted amount of platelets or the targeted amounts of platelets and plasma have been collected, the system may transition to a phase in which a platelet additive solution is added to the collected platelets, as shown in FIG. 6. To this end, clamps 15 and 17 open. PPP pump 6 draws PAS out of PAS bag 71 through open clamp 17, line 63, plasma sensor 27, and back through spinning membrane 101 into line 55, line 56, open clamp 15 and PC product bag 70. PAS is added until a desired volume in PC bag is reached.

d. MNC Harvest and Storage

Figure 7:
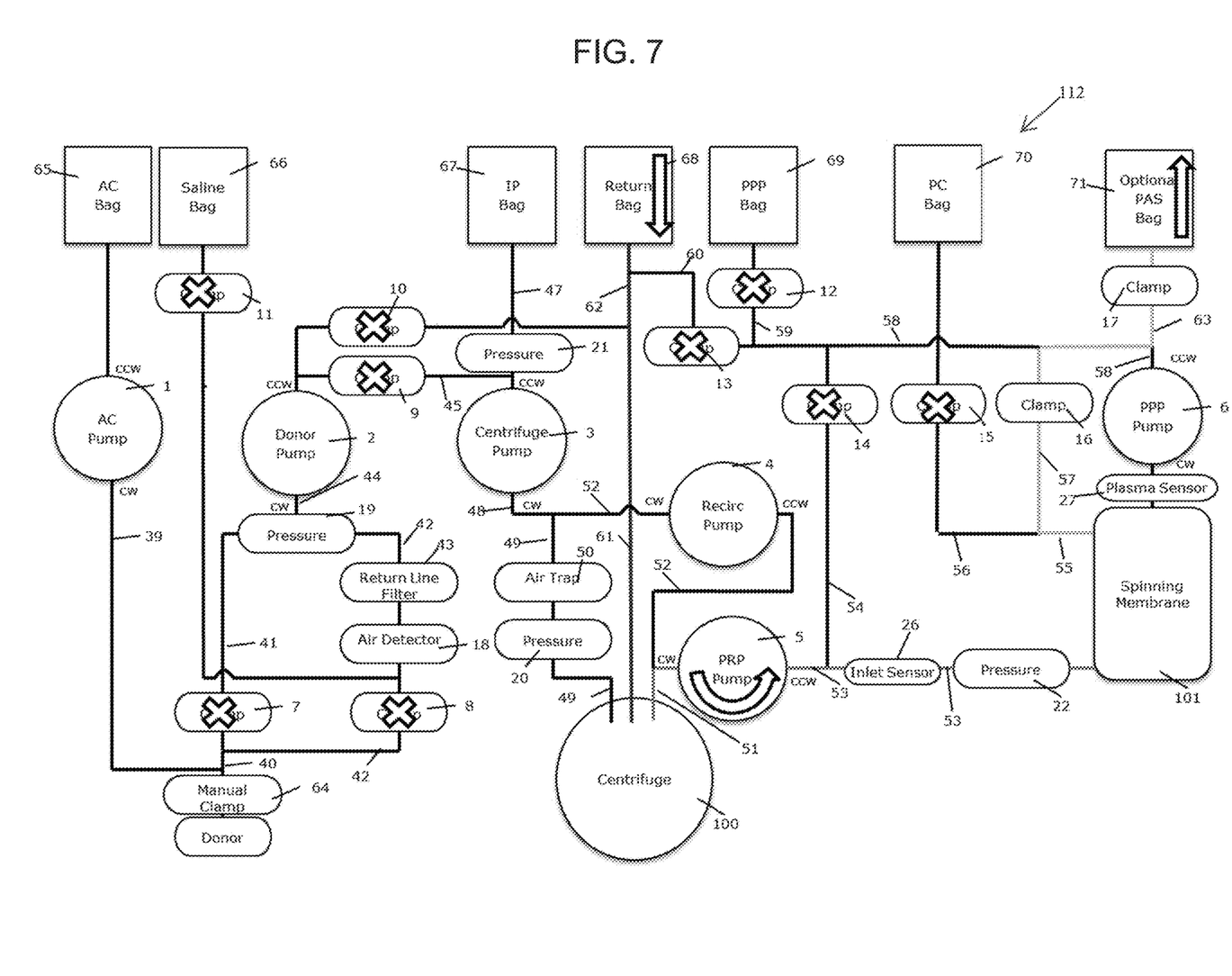
FIGS. 7-9 depict the first, second and third phases, respectively, for harvesting the MNCs.
Figure 8:
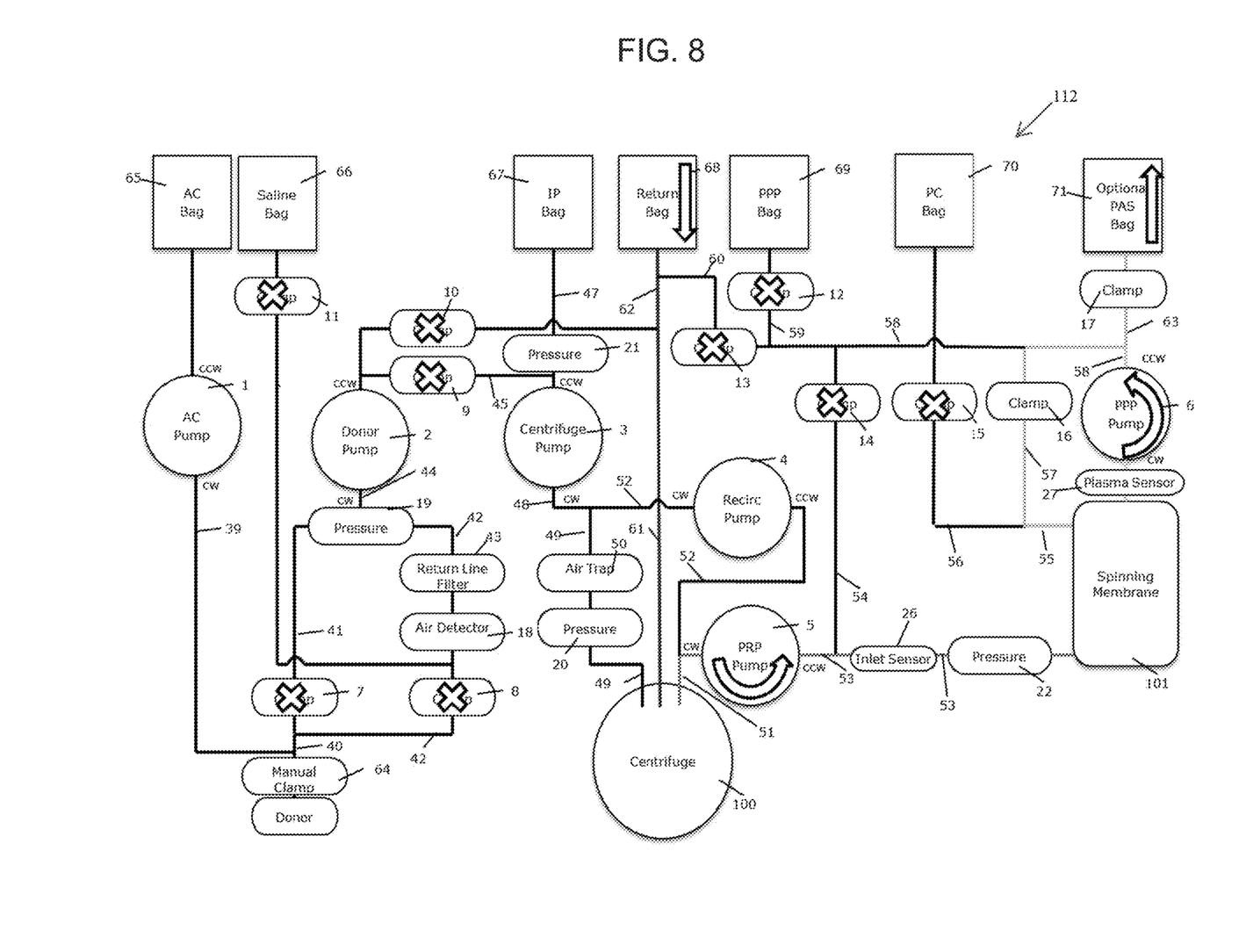

Upon completion of the platelet collection phase, but prior to the kit reinfusion phase which returns the remaining contents within the disposable kit to the donor, the MNC layer within the centrifuge chamber can be harvested, as shown in FIG. 7.

The thickness of the RBC bed in the centrifuge must be increased to push the MNCs which have built up in between the RBC and PRP layers towards the PRP outlet of the centrifuge 100. To do so, the RBCs which were collected into return bag 68 are pulled through line 62 and line 61 into the centrifuge 100 by PRP pump 5. The centrifuge rotation remains at the nominal rate, such as 4500 rpm, throughout the transfer. The RBCs entering the centrifuge 100 will quickly increase the thickness of the RBC bed causing the MNCs on top of the RBC layer to exit through PRP line 51. Both centrifuge pump 3 and recirculation pump 4 are stopped, thus preventing fluid from exiting line 49.

The MNCs are pulled out of the centrifuge and into line 51 by PRP pump 5. The MNCs then travel through line 53, sensor 26, pressure sensor 22, and into spinning membrane separator 101. Fluid present in spinning membrane separator 101, which may be residual plasma, platelets, or PAS, is pushed out of the spinner 101 into line 55, line 58, line 63 and into the PAS bag 71 (which now acts as a waste bag).

The optical sensor 26 placed on line 53 is used to detect the optical density and/or the redness (depending on sensing method applied) of the fluid exiting the centrifuge. At the start of the MNC transfer the fluid may contain mostly platelets exhibiting a low optical density and little redness. As the phase continues and more RBCs are pumped into the centrifuge 100 increasing the RBC bed thickness, the concentration of RBCs exiting the centrifuge 100 through line 51 will continue to increase. Once the optical density or redness as detected by sensor 26 reaches a specific experimentally-predetermined threshold, the MNC transfer phase will be complete. The MNC transfer would be optimized to ensure a majority of the MNCs enter the spinner but do not exit line 55. Specifically, flow rates out of the centrifuge and into/out of the spinner, and the duration of those flow rates and thus the volume, would be set to ensure that MNCs are not being pumped out of the spinner via line 55. For example, if the MNCs are going to exit the centrifuge over a 10 ml span, a pump rate of 5 to 10 ml/min may be set and the pump run for 1 min to move 10 ml of fluid (containing MNCs) to the spinner. At this point the MNC product will be completely contained within the spinner 101.

During the transfer of MNCs to the spinning membrane separator, fluid is not passing through the membrane. Thus, the cellular content in the spinning membrane is not being concentrated. However, it may be desirable to concentrate the MNCs exiting the centrifuge. This can be accomplished by filtering plasma through the membrane using PPP pump 6. During this phase, shown in FIG. 8, PPP pump 6 is initiated to draw plasma through the membrane and inline line 58, line 63, and PAS bag 71 (waste bag). Since only plasma can pass through the membrane, MNCs will be left behind in the spinner annulus in a more concentrated form. The rate at which fluid exits the spinner via line 55 is equal to the difference of the PRP pump 5 and PPP pump 6.

Figure 9:
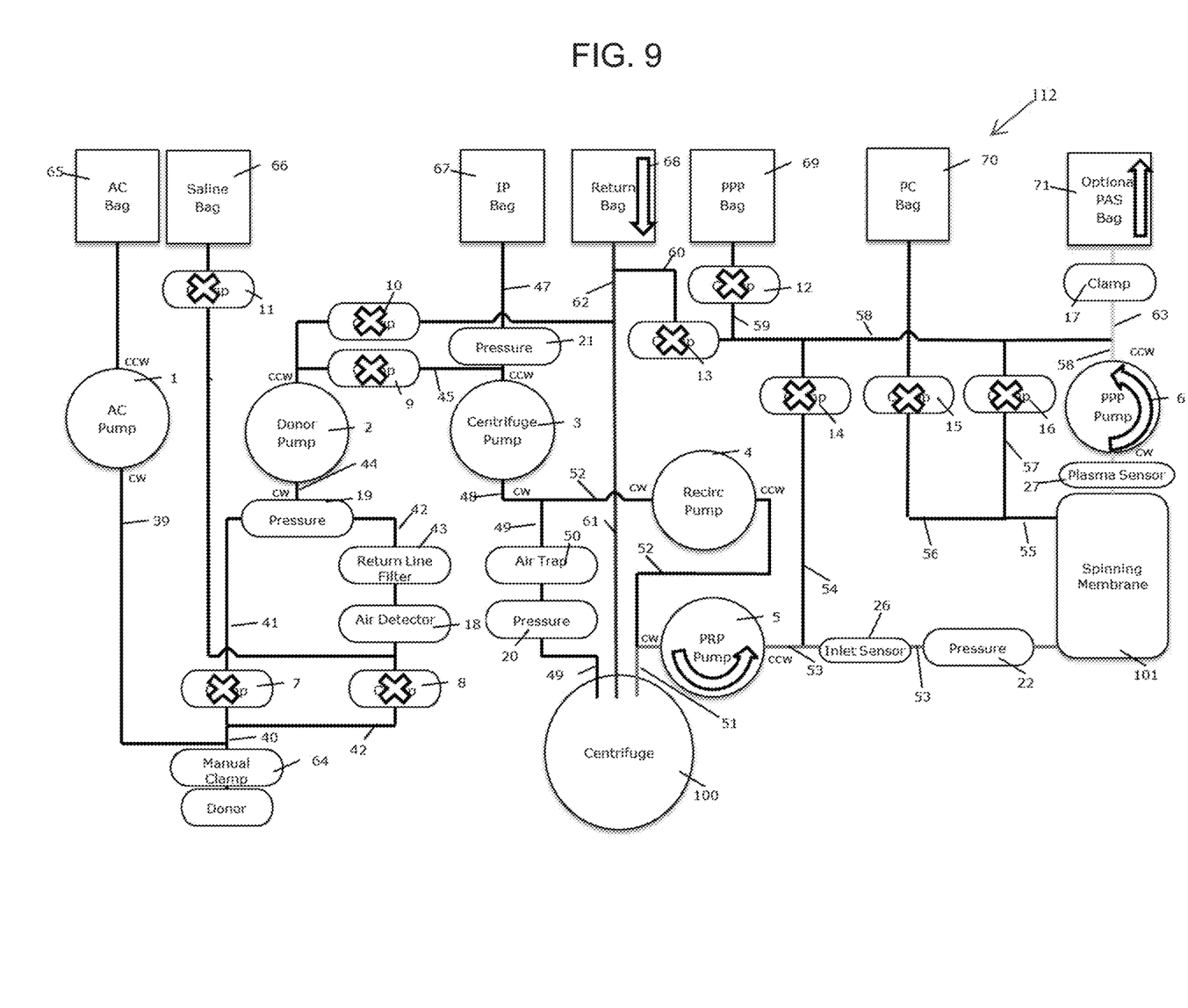

A third phase may also be applied in which clamps 15 and 16 are closed to prevent fluid flow out of the spinner via line 55. PPP pump 6 is set equal to PRP pump 5, and plasma is pulled through the membrane into line 58, line 63, and PAS bag 71 (waste bag). This phase creates a super-concentrated MNC product within the spinner annulus, since all of plasma suspension entering the spinner with the MNCs is being filtered through the membrane and out of the spinner.

Seals can then be made on lines 53, 55, and 58, and the spinner containing MNCs disconnected from the device. A user may then drain the contents of the spinner into a bag to serve as a cell source for research, or a user may attach the spinner with MNCs to a dedicated cell washing kit and perform a cell washing procedure to purify the MNC product, as is typically done at the onset of a research protocol.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein.

The invention claimed is:

1. A method for harvesting mononuclear cells (MNCs) during a platelet collection procedure comprising:
 a) withdrawing whole blood (WB) from a blood source;
 b) introducing WB into a centrifugal separator;
 c) separating WB within the centrifugal separator into platelet rich plasma (PRP), packed red blood cells (RBCs) containing white blood cells (WBCs) and a WBC layer including MNCs;
 d) flowing PRP to a spinning membrane separator;
 e) flowing a first quantity of RBCs and WBCs to a return container;
 f) retaining a second quantity of RBCs and the WBCs, including MNCs, within the centrifugal separator;
 g) separating PRP within the spinning membrane separator into platelet poor plasma (PPP) and platelet concentrate (PC);
 h) flowing the PPP to one of the return container and a first collection container;
 i) flowing the PC to a second collection container;
 j) flowing RBCs, or RBCs and PPP, from the return container to the centrifugal separator in an amount sufficient to push the MNCs out of the centrifugal separator;
 k) flowing the MNCs to the spinning membrane separator; and
 l) sealing the spinning membrane separator to retain the MNCs therein.

2. The method of claim 1 further comprising flowing PPP from the spinning membrane separator after step k) to concentrate the MNCs within the spinning membrane separator.

3. The method of claim 1 further comprising adding platelet additive solution (PAS) to the second collection container after the PC has been flowed thereto.

4. The method of claim 1 further comprising detecting whether a specified optical density of RBCs are exiting the centrifugal separator, and stopping step j) upon detecting the specified optical density of RBCs exiting the centrifugal separator.

5. The method of any of claim 1 wherein the spinning membrane separator is part of a disposable fluid flow circuit, the method further comprising detaching the sealed spinning membrane separator from the fluid flow circuit.

6. A blood separation system comprising:
 a disposable fluid flow circuit comprising a centrifugal separation chamber, a spinning membrane separator, a return container, a first collection container, and a second collection container, all interconnected by tubing to permit fluid flow therebetween; and a hardware component comprising a centrifugal separator configured to receive the centrifugal separation chamber of the fluid flow circuit, a spinning membrane separator drive unit configured to receive the spinning membrane separator of the fluid flow circuit, and a controller configured and/or programmed to control the operation of the centrifugal separator and the spinning membrane separator drive unit, wherein the controller is configured and/or programmed to automatically a) withdraw whole blood (WB) from a blood source, b) introduce the WB into the centrifugal separation chamber, c) separate the WB within the centrifugal separation chamber into platelet rich plasma (PRP), packed red blood cells (RBCs) containing white blood cells (WBCs), and a WBC layer including mononuclear cells (MNCs), d) flow PRP from the centrifugal separation chamber to the spinning membrane separator, e) flow a first quantity of RBCs and WBCs from the centrifugal separation chamber to the return container, f) retain a second quantity of RBCs and the WBCs, including MNCs, within the centrifugal separation chamber, g) separate the PRP with the spinning membrane separator into platelet poor plasma (PPP) and platelet concentrate (PC), h) flow the PPP from the spinning membrane separator to one of the return container and the first collection container, i) flow the PC from the spinning membrane separator to the second collection container, j) flow RBCs, or RBCs and PPP, from the return container to the centrifugal separation chamber in an amount sufficient to push the MNCs out of the centrifugal separation chamber, k) flow the MNCs to the spinning membrane separator, and l) retain the MNCs in the spinning membrane separator.

7. The blood separation system of claim 6 wherein the controller is further configured and/or programmed to automatically: m) flow PPP from the spinning membrane separator to concentrate the MNCs within the spinning membrane separator.

8. The blood separation system of claim 6 wherein the disposable fluid flow circuit further comprises a source of platelet additive solution (PAS) and the controller is further configured and/or programmed to automatically flow PAS to the second collection container after the PC has been flowed thereto.

9. The blood separation system of claim 6 wherein the hardware component further comprises a sensor for detecting whether a specified optical density of RBCs are exiting the separation chamber and the programmer is further configured and/or programmed to automatically stop the flow RBCs, or RBCs and PPP, from the return container to the separation chamber upon detection of the specified optical density of RBCs exiting the separation chamber.

* * * * *